United States Patent [19]

Still

[11] Patent Number: 5,038,047
[45] Date of Patent: Aug. 6, 1991

[54] RADIATION SHIELD HOOD FOR THE HEAD AND NECK

[76] Inventor: Shirley S. Still, 680 W. Rose St., Lebenon, Oreg. 97355

[21] Appl. No.: 495,897

[22] Filed: Mar. 19, 1990

[51] Int. Cl.$^5$ .............................................. G21F 3/02
[52] U.S. Cl. .............................. 250/516.1; 250/519.1; 250/515.1; 128/857; 128/858; 2/15; 2/410; 2/422; 2/424
[58] Field of Search ............... 250/515.1, 516.1, 519.1; 128/857, 858; 2/410, 422, 424, 15

[56] References Cited

U.S. PATENT DOCUMENTS

| | | | |
|---|---|---|---|
| 2,451,282 | 10/1948 | Feibel | 250/108 |
| 2,717,437 | 9/1955 | de Mestral | 2/DIG. 6 |
| 2,857,525 | 10/1958 | Ferdon | 250/516.1 |
| 3,030,628 | 4/1962 | Crosson | 351/44 |
| 3,189,917 | 6/1965 | Sims | 2/3 |
| 3,233,248 | 2/1966 | Bushnell | 2/2 |
| 3,996,620 | 12/1976 | Maine | 2/2 |
| 4,021,862 | 5/1977 | Glasser et al. | 2/431 |
| 4,024,405 | 5/1977 | Szot | 250/516.1 |
| 4,196,355 | 4/1980 | Maine | 250/516.1 |
| 4,220,867 | 9/1980 | Block | 250/516 |
| 4,223,229 | 9/1980 | Persico | 250/515.1 |
| 4,386,277 | 5/1983 | Forshee | 250/516.1 |

Primary Examiner—Jack I. Berman
Attorney, Agent, or Firm—Charles Hilke

[57] ABSTRACT

A lead impregnated shielding material hood to protect the head, brain, hypothalamus, and the master glands. A radiation protective shield for preventing direct impingement of radiation rays on the brain, neck, some salivary glands, thyroid and the adjacent body areas of head and eyes and adjacent tissues, of the patient being x-rayed. Having extraoral portion being of shape and size to cover the lead impregnated shielding material, and a substantial area of the extraoral anatomy of the head of the person to thereby intercept rays and prevent direct and/or stray penetration impingement thereon. Having physically protection of the parotid, sublingual and salivary glands. A radiation protective lead impregnated shielding hood shield being to prevent head and eyes from contact with x-rays or secondary x-rays which involve substantially large or intense radiation treatments.

7 Claims, 1 Drawing Sheet

U.S. Patent  Aug. 6, 1991  5,038,047
FIG. 1
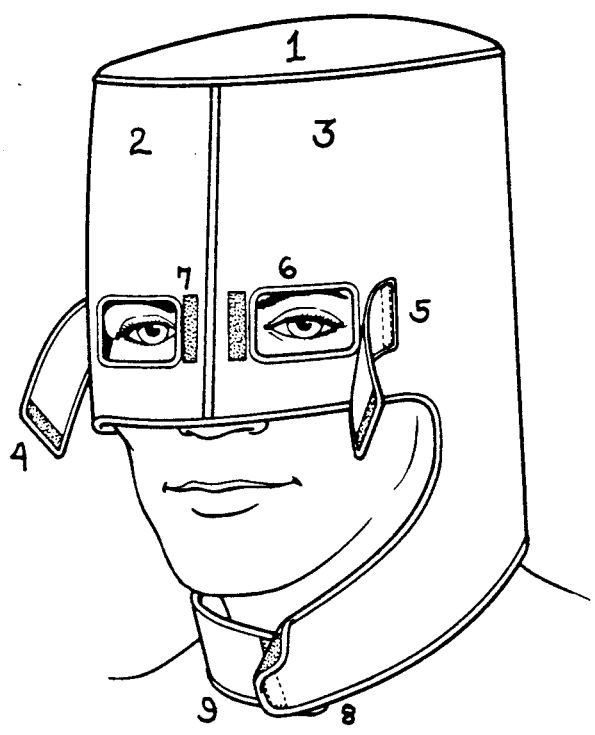
FIG. 2
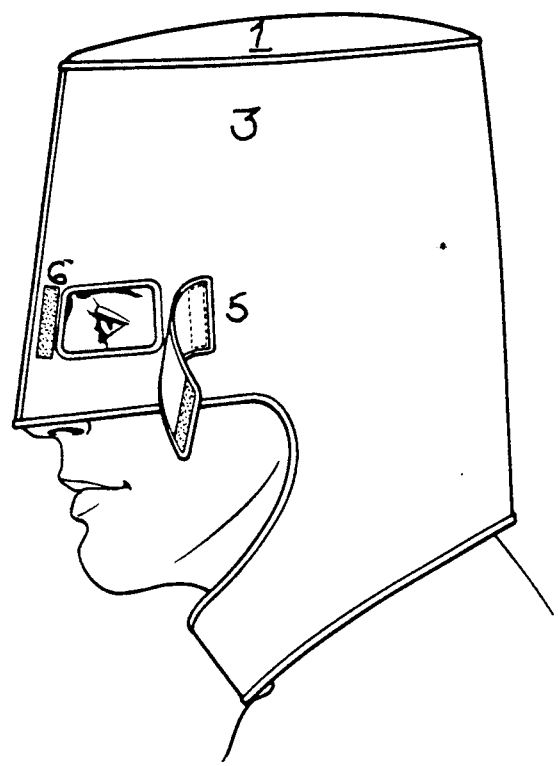
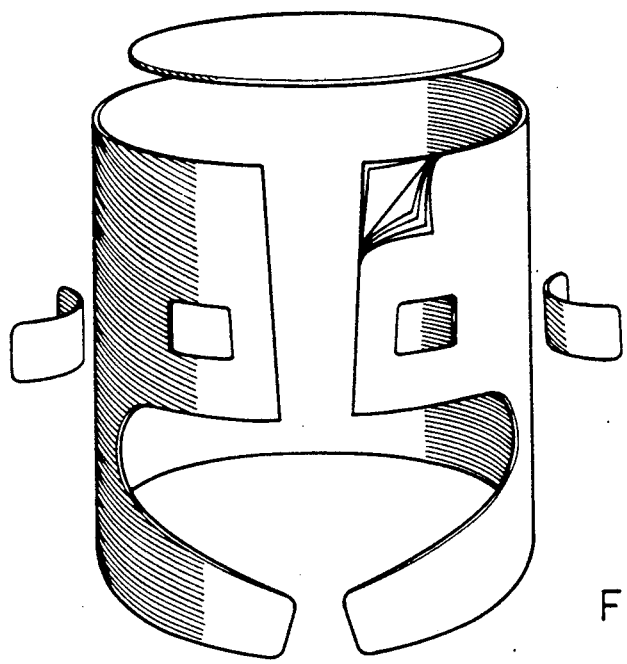
FIG. 3
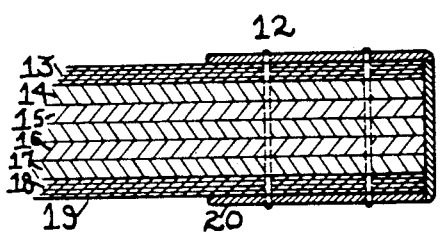
FIG. 4
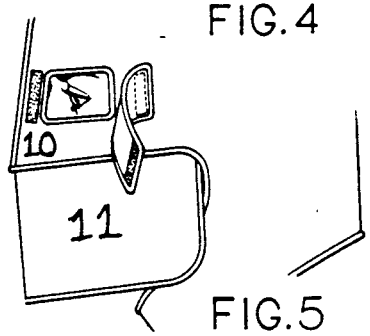
FIG. 5

RADIATION SHIELD HOOD FOR THE HEAD AND NECK

BACKGROUND

Congress has declared the 1990's the "decade of the Brain." Therefore we must shield the brain from harmful primary and secondary x-rays. The brain has 10 billion cells linked by a trillion electrical connections, highly organized and more sophisticated than a NASA shuttle. The human brain quietly directs every breath, every thought, work and deed of every person on earth. "Views" magazine, Oregon State University, Winter 1990.

There is an increasing awareness in the medical, dental and veterinary fields of possible serious damages that can be inflicted on gingiva, teeth, dentition, periodontal bone; parotid, sublingual and salivary glands, and other related body cells and organs as these areas of dentition are very susceptible to the effects of radiation and the harmful side effects of therapeutic practice in treating cancer patients; particularly when the patient receives large and intense radiation doses of 2500–5000 rem to the head and neck region. Thyroid treatments often require 5000 rem as well.

Fluoroscopy in cardiovascular analysis or treatment is utilized by insertion of dye containing catheters or probes into main arteries and other passages under precisely controlled conditions aiding in dental, medical and veterinary diagnostics.

The use of x-rays for diagnostic purposes in dentistry have been of great concern. Research has usually cautioned the medical and dental professions to avoid unnecessary exposure of patients to x-rays. X-rays are detrimental and dangerous and do have an accumulative effect. AMA The nerve cells, or neurons, and the cells that appeared blue between the nerve cells, called neuroglia, all individual cells, work together to perform the work in the brain.

The central nervous system.

The brain controls your breathing to maintain just the right amounts of oxygen in your bloodstream, as well as your blood pressure to keep the fresh oxygenated blood going to your head.

The nutrient content in your bloodstream, that provided one of the signal to eat again.

The body temperature to the amount of water your body needs to stay in balance.

The hormonal control of you.

Vision can be influenced by radiation effects on the retina. The optic nerve is located in the brain the thalamus and hypothalamus.

The hearing can be affected by radiation.

The cochlear nerve and cochlea.

Auditory cortex cochlea.

The brain attributed the sensation, motion, internal regulation, reproduction and just adaption to our surroundings.

There are glands which might be otherwise permanently damaged from treatment from x-rays thereto; such as parotid, carotid arteries, lymph glands, as well as the thyroid gland and the like—BRAIN.

The danger is well recognized and some states are requiring that the reproductive organs be protected against stray x-radiation during the course of x-ray examination or treatment.

It is known that radiation and in particular x-rays produce some effect on every living cell. It is also known that those cells which do not divide, such as the nerve cells within the brain and also those cells that divide very slowly such as those that make up the muscles, can withstand considerably more radiation than cells which are continually dividing to produce new ones.

The various glands including the thyroid, parathyroid, thymus, adrenal and suprarenal are very sensitive to x-radiation. It is important, therefore, that all patients, doctors, and ancillary staff subjected to x-rays be protected against such undesirable radiation. The danger is well recognized. The pituitary gland regulates the body's growth pattern.

SUMMARY

The primary purpose present invention is to provide a patented shielding hood and collar and apparatus/device that will overcome many of the existing problems and help both the wearer and the medical and dental personnel, and veterinarians from x-ray radiation to brain, eyes, mouth and thyroid. The lead impregnated shielding hood can shield the patients eyes, brain and mouth with the collar in an open position during the radiation treatment.

The lead impregnated protective hood or shielding device greatly minimizes possible injury to the patient from scattered and primary surplus x-rays, contacting tissues other than those which are intended to be subjected to the x-rays. Shield patients and/or certain body areas from stray x-rays during diagnostic and radiotherapy treatment for either the wearer or the medical or dental professional performing the treatment. If during operation in surgery to protect all medical staff in the surgery room. The neck of the hood will fit around the patient's or wearer's neck and maximum shielding protection of patients and ancillary staff who have to remain in the room, during an operation.

The primary object of this invention is to provide a device for protecting the wearers head, brain and neck from harmful primary and secondary x-rays, be it dental, therapeutic, medical or veterinarian.

Another object of this invention is to provide shielding to the eyes of the wearer to harmful x-ray to the eyes.

Another object of this invention is to provide protection to the mouth, the salivary glands, the teeth, etc. of the wearer.

Another object of this invention is to provide protection to the thyroid glands.

DESCRIPTION OF DRAWINGS

FIG. 1 is a front view illustration of a human head with the Lead Impregnated Radiation Shield Hood in operative position, showing Velcro S. A. Switzerland sewed closure tabs in place to afford eye shielded from the x-rays.

FIG. 2 is a side view of human head with the Lead Impregnated Radiation Shield Hood with lead impregnated shielding material eye flap material open.

FIG. 3 is an exploded front view of the Lead Impregnated Radiation Shield Hood. This showing the multiple layers of lead impregnated shielding material.

FIG. 4 is an enlarged out-away illustration showing the multiple layers of radiation shielding material, and stitched edge binding.

FIG. 5 is a side view illustration of the attached eye shielding device and the optional mouth guard in position modification to the hood using when wearer is not being x-rayed for dental bite wing x-ray or intraoral x-rays. This mouth guard can be positioned by wearer when not having dental bite wing or intraoral x-ray.

DETAILED DESCRIPTION OF A PREFERRED EMBODIMENT

Referring initially to FIGS. 1 and 2 of the drawing; a hood comprises the lead impregnated material of the hood and thyroid shielding device.

This hood includes a usual eye, nose and neck opening. This facilitates for oral x-rays, yet with the eye flaps, engages and can afford shielding to the eyes.

FIG. 3 is a cut away drawing showing a number of flexible layers of lead impregnated material. These inner sheets comprise multiple layers of flexible lead sheeting, the number of sheets used being determined by the degree of protection desired. For example one flexible lead sheet of 0.015 mm thickness is equal to 0.01 mm thickness of pure lead.

FIG. 4 thus if 0.05 mm of lead protection is required, five layers of the flexible lead sheet of the desired thickness are used in the hood.

Layers 13 and 19 are washable vinyl or other suitable material.

Layers 12 and 20 are binding tape of appropriate material.

Layers 14, 15, 15, 17, 18 are layers of lead impregnated sheets, usually 0.015 mm thickness.

FIG. 5 is side version of shielding hood with #11 mouth shielding device being held in place by Velcro S. A. #10 tabs holding #11 mouth guard in place for #10 Velcro.

Layers 8 and 9 are Velcro S. A. closures bands to ensure rapid and easy attachable closure for the neck thyroid closure.

Layers 4 and 5 eye closure are complementary closures of the lead impregnated shielding devices in place.

Layers 6 and 7 are the mating closures for 4 and 5 also #10 for the mouth shielding device.

METHOD OF CONSTRUCTION

The preferred embodiment of the present invention consists of —0.25 or 0.5 mm lead equivalent material such as in Main U.S. Pat. No. 3,093,829 hood ban be made in several sizes to fit the wearer.

The body of the hood consists of lead impregnated material pliant, flexible, multi-layer body of sheet material 0.3 mm or 0.5 mm lead equivalency bonded to a supporting sheet of thinner material.

Sew hood center/front seam together with appropriate thread thickness stitching firmly through the several layers of the lead impregnated material.

Stitch the crown section to the hood.

All said sheets of the lead impregnated material should be permanently fastened together along their perimeter by suitable material extending around the perimeter of the edges of the hood and stitched in place. The outer sheet of material can be of vinyl or material suitable for sanitation.

The eye windows are also stitched with appropriate and suitable binding.

Pairs of complimentary adhering closure tabs are sewed or cemented to sides of the eye and mouth guard opening in a vertical band. The tabs are known and may be made of tape of the type manufactured by Velcro, S. A. of Switzerland. The closure tabs are on the center area of the eye openings. The mating tabs are shown attached to the end of the eye openings, thus the protective shielding eye and material guards can be placed across the eye attached with Velcro S. A. with the shielding guard held in place over the eye.

In like manner, the mouth shielding guard can be held in place by horizontally attaching the mouth guard to the hood using Velcro S. A. closure tabs to allow closure if the wearer desires.

The thyroid section of the hood is also closed and secured by Velcro S. A. closure tabs at the chin and neck section of the hood.

While the device herein described constitutes a preferred embodiment of the invention, it is to be understood that the invention is not limited to this precise form of device and that changes may be made therein without departing from the scope of this invention which is defined in the appended claims.

I claim:

1. A multi-layered pliant hood comprising lead impregnated material adapted to cover a wearer's head and neck, two openings in said material in locations corresponding to a wearer's eyes, and eye flaps of the same lead impregnated material releasably secured to said hood to selectively cover or uncover said openings.

2. A hood as set forth in claim 1 wherein said eye flaps are secured by Velcro.

3. A hood as set forth in either of claims 1 or 2 and further comprising a third opening in said material in a location corresponding to a wearer's mouth.

4. A hood as set forth in claim 3 and further comprising a mouth guard of lead impregnated material releasably secured to said hood so as to cover said third opening.

5. A hood as set forth in claim 4 wherein said mouth guard is secured to said hood by Velcro.

6. A hood as set forth in claim 3 and further comprising a neck closure comprising two closure bands between said third opening and a bottom edge of said hood, said closure bands being mutually engageable so as to selectively cover or expose a wearer's thyroid gland.

7. A hood as set forth in claim 6 wherein said closure bands comprise Velcro.

* * * * *